United States Patent [19]
Zardi et al.

[11] Patent Number: 5,176,800
[45] Date of Patent: Jan. 5, 1993

[54] PROCESS FOR THE MODERNIZATION OF EXISTING UREA PLANTS AND A MODERNIZED UREA PLANT

[75] Inventors: Umberto Zardi, Via Lucino 57, CH-6932 Breganzona: Giorgio Pagani, Lugano, both of Switzerland

[73] Assignees: Ammonia Casale S.A.; Umberto Zardi, both of Switzerland

[21] Appl. No.: 634,410

[22] Filed: Dec. 27, 1990

[30] Foreign Application Priority Data

Dec. 29, 1989 [CH] Switzerland ................. 04671/89

[51] Int. Cl.⁵ ..................... B01D 3/00; C07C 273/16
[52] U.S. Cl. ..................... 203/31; 159/47.2; 203/49; 203/73; 203/80; 564/68; 564/71; 564/72; 564/73
[58] Field of Search ........... 203/31, 73, 49, 80, 203/1, DIG. 18; 564/71, 68, 72, 73; 159/47.2; 423/358

[56] References Cited

U.S. PATENT DOCUMENTS

| | | | |
|---|---|---|---|
| 1,986,973 | 1/1935 | Hetherington et al. | 564/68 |
| 3,488,293 | 1/1970 | Hong et al. | 564/68 |
| 4,269,997 | 5/1981 | Pastormerlo | 564/67 |
| 4,301,299 | 11/1981 | Inoue et al. | 564/67 |
| 4,308,385 | 12/1981 | Goorden | 423/358 |
| 4,540,813 | 9/1985 | Van Nassau | 564/71 |
| 4,747,915 | 5/1988 | Pagani | 159/47.2 |
| 4,758,311 | 7/1988 | Pagani et al. | 159/49 |
| 4,801,747 | 1/1989 | Jonckers | 564/73 |
| 4,866,207 | 9/1989 | Jonckers et al. | 564/73 |

FOREIGN PATENT DOCUMENTS

| | | | |
|---|---|---|---|
| 96151 | 7/1986 | European Pat. Off. | |
| 0221176 | 4/1985 | Fed. Rep. of Germany | 564/73 |
| 0925936 | 5/1982 | U.S.S.R. | 564/73 |
| 1341497 | 12/1973 | United Kingdom | 203/7 |
| 8002425 | 11/1980 | World Int. Prop. O. | 564/73 |

OTHER PUBLICATIONS

European Chemical News; Jan. 17, 1969 ("Urea Supplement") pp. 17, 19, 20.
Belgian Patent 625397, Belgian Report Dec. 1963.

*Primary Examiner*—Virginia Manoharan
*Attorney, Agent, or Firm*—Ostrolenk, Faber, Gerb & Soffen

[57] ABSTRACT

A process to modernize existing urea plants which use a stripping with carbon dioxide, and to increase urea yields and flexibility under overload conditions while at the same time reducing energy consumption, corrosion phenomena and possible risks of explosive mixtures. The plant includes: a passivation stage with the introduction of an oxidizing agent and reduction of the air fed to the system; a medium pressure distillation stage of the products leaving the stripping section, and a condensation of the products of the distillation, effected in a pre-evaporation phase to concentrate at low pressure the urea solution.

The modernized plant, includes at the start at least a reactor, a scrubber, a condenser, a stripper and the evaporators, includes also a passivation section, a medium pressure distillation section, and a distillation section with double-effect technique.

7 Claims, 2 Drawing Sheets

PROCESS FOR THE MODERNIZATION OF EXISTING UREA PLANTS AND A MODERNIZED UREA PLANT

BACKGROUND OF THE INVENTION

This invention concerns a process for the modernization of existing urea plants, and more particularly to increase urea yields, reduce energy consumption, inhibit corrosion phenomena and make the operation flexible under overloading conditions. Product leaving the reactor for the synthesis of urea from ammonia (NH3) and carbon dioxide (CO2) is stripped with one of the reagents, more particularly with CO2, the carbamate is condensed in a condenser and the vapors are treated at high pressure in a scrubber.

The invention also concerns the plants so improved in situ.

DESCRIPTION OF THE RELATED ART

As is well known in the synthesis of urea, aqueous solutions of urea are produced containing unreacted compounds and more particularly ammonium carbamate and NH3 which must be treated downstream to decompose the carbamate and recover the urea solutions as well as the unreacted ammonia and CO2.

More particularly, in the greater part of existing urea plants at least one stripping of the effluents from the reactor is carried out using as stripping agent at least one of the two reagents (CO2 or NH3).

The major characteristics of the numerous plants of the first type (CO2) can be summarized as follows:
- the flow of CO2 being fed to the reactor is used as agent to remove said unreacted products;
- synthesis pressure is relatively low (for example, 140 bar);
- the major part of the residual carbamate in the stripper operating at the same pressure as the synthesis reactor is removed;
- a single carbamate recycle stage at low pressure, for example between 3.5 and 4.5 bar;
- consumption of medium pressure steam for the process of the order of 900–1000 kg/MT of urea.

FIG. 1 shows a scheme indicating the most important sections of the existing plants with CO2 as stripping agent.

R indicates the reactor fed through line 1 and the condenser CO.CA with NH3, and through line 2 and stripper ST with CO2.

SCRU indicates the high-pressure scrubber, DECO is the decomposer fed through line 3 from stripper ST.

By way of example, the most significant operating conditions can be summarized as follows:

| | |
|---|---|
| molar ratio NH3/CO2 in the reactor | 2.8 |
| molar ratio H2O/CO2 in the reactor | 0.4 |
| conversion yield of CO2 into urea in the reactor | 57% |
| temperature of reactor effluent | 183° C. |
| pressure in the reactor | 141 bar |
| steam consumption at 20 bar | 930 kg/MT urea for the stripper; 70 kg/MT for the second urea concentrator |
| exported steam | 4.5 bar |

This process has the advantage of operating at not very high synthesis pressure, of having an efficient recycle of unreacted substances directly to the reactor and of requiring a reduced number of finishing stages, due to the efficiency of the stripping with CO2.

However, this process has a relatively high heat consumption (steam) and little flexibility in operation due to the presence of a single low pressure distillation stage before the vacuum section.

This stage is operated with difficulty when the performance of the stripper gets worse (for example by overloading the stripper) and thus the amount of unreacted substance (NH3 and CO2) to be sent to the LP stage increases.

Besides, in order to inhibit corrosion phenomena in the stripper, in the carbamate condenser and in the high pressure scrubber, a relatively large amount of air (above 6000 ppm with reference to the CO2) is added, for example to the feed CO2 to be able to passivate the above equipment.

This anomalous amount of air (and thus inert gas) makes it compulsory to operate with low NH3/CO2 ratio in the reactor, with the result of low yields and relatively high steam consumption.

The above problems get more acute when the plant must operate under overloaded conditions, hence the unsuitability of the process to operate under harder conditions than those planned for in the design.

SUMMARY OF THE INVENTION

The object of this invention is to eliminate the above disadvantages, and more particularly to increase yields, reduce energy consumption, corrosion phenomena and the danger that explosive mixtures may form, as well as to make the process more flexible, as required by the plans for the modernization of urea production plants of this type.

It has been found, not without surprise, that it is possible to eliminate the drawbacks mentioned above (such as low conversion yield, high energy consumption, corrosion phenomena, little operational flexibility) by adopting in situ a few simple measures, and more particularly at least those concerning:
- the drastic reduction of the amount of passivating air, for example to about 1/3 of the design amount, compensating for the lack of oxygen preferably in the stripper and in the carbamate condenser by means of injecting small amounts of an oxidizing agent in the liquid phase upstream of the equipment to be passivated; the feed of H2O2 and the resulting reduction of air are carried out in the PASS section. In pre-existing plants the passivating air is equal to amounts of between about 6000 and 8000 ppm referred to the feed CO2;
- the increase of excess NH3 in the reactor of between 2.8 mol and 3.4 mol, due to the reduction of inerts (air) and therefore increase of the reactor conversion yield;
- the addition of a medium pressure (MP) distillation stage capable of reducing the heat load of the upstream stripper (ST) and of the low-pressure downstream distiller (LP), with the resulting possibility of overloading these two pieces of equipment.

In a particularly advantageous and therefore preferred embodiment of the invention, the new distiller MP is connected, according to the technique of double effect, to a new vacuum pre-distiller in which vapors MP condense with the consequent partial distillation of the urea solution. This combination makes it therefore possible to use the heat transferred to the new MP distillator twice, with an appreciable reduction of energy consumption.

It can therefore be seen that by operating according to the invention it is possible to debottleneck in a surprisingly simple manner the key synthesis sections and those of distillation and recycle of the stripping process with CO2, making it technically workable and financially feasible to modernize this type of plant.

DETAILED DESCRIPTION OF THE PREFERRED EMBODIMENTS

Figure 1:
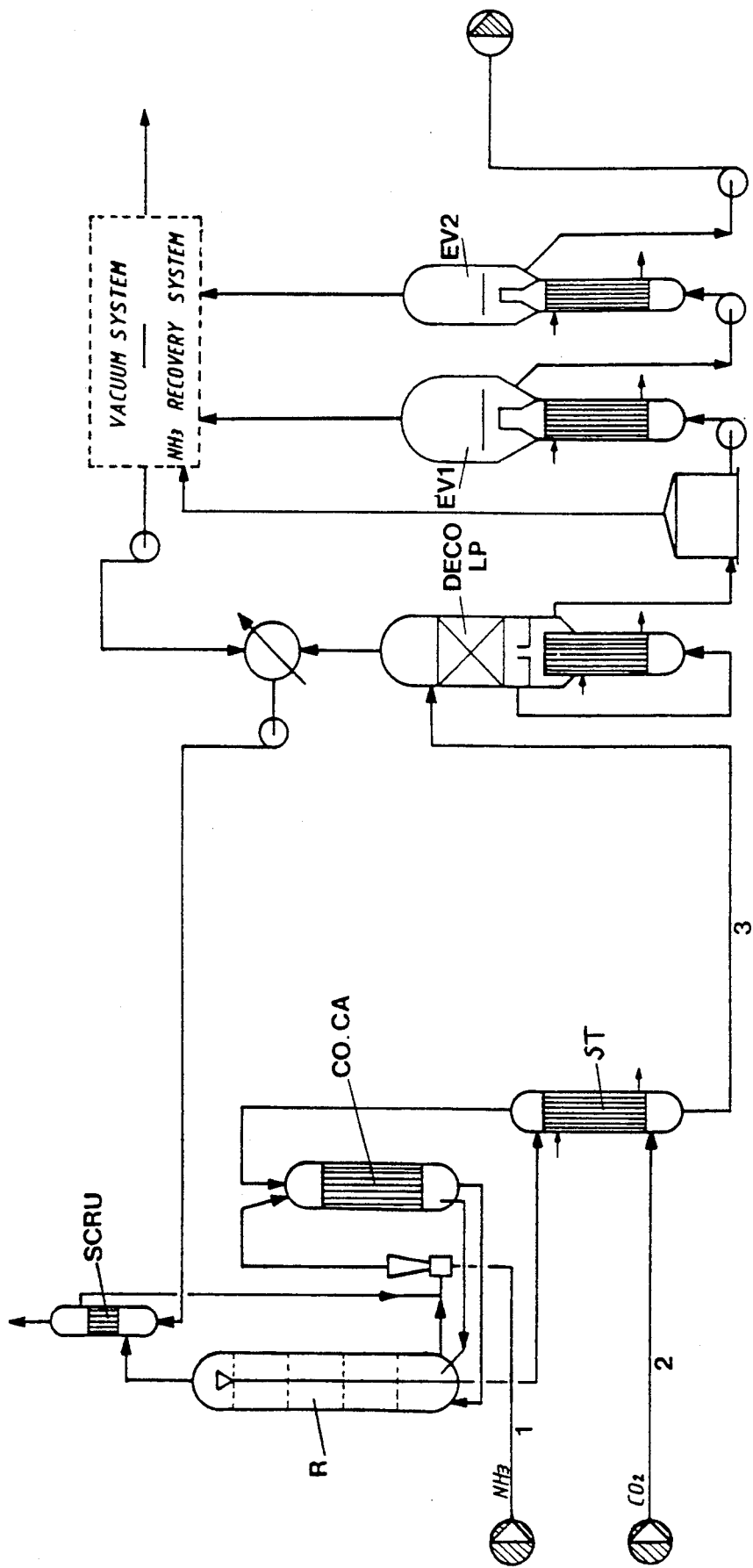
FIG. 1 shows a prior art process and plant.
Figure 2:
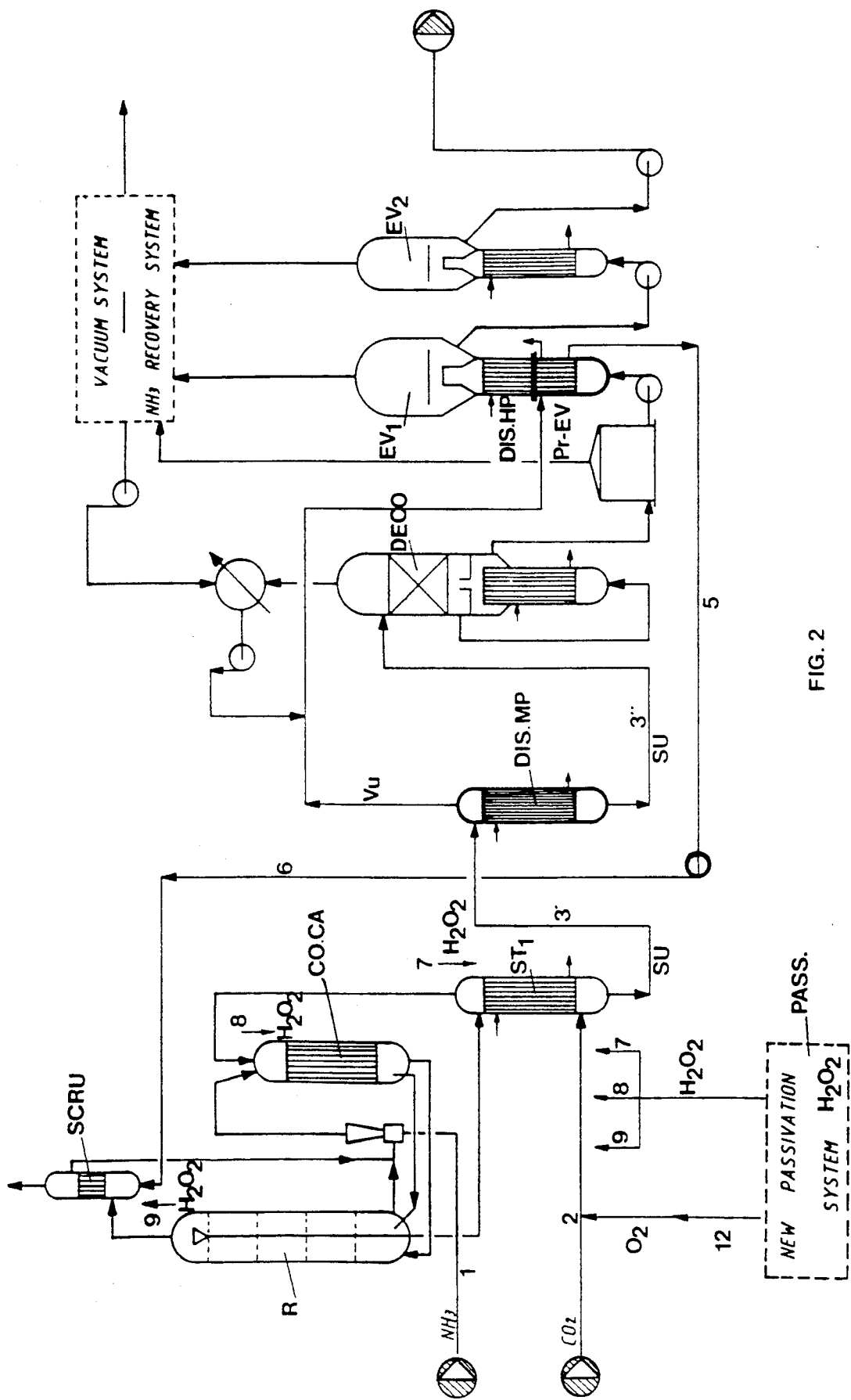
FIG. 2 shows the flow sheet for the process and for the plant modified according to the invention.

The top high pressure (H.P.) part, comprising the reactor (R), stripper (ST), carbamate condenser (CO.CA) and H.P. scrubber (SCRU) remain unchanged. According to a first aspect of the invention however their operating conditions change, for example as follows:
- the flow of passivating air, which in pre-existing plants varies between 6000 and 8000 ppm of O2 with respect to the CO2, is now drastically reduced, for example to ⅓ of the design value (line 12);
- the NH3/CO2 ratio in the reactor is therefore increased to for example 3.4 mol;
- the ratio H2O/CO2 in the reactor is 0.5 mol;
- conversion Yield of CO2 into urea in the reactor is 72%;
- the stripper (ST), carbamate condenser (CO.CA) and H.P. scrubber (SCRU) ar passivated for example with H2O2 through lines 7, 8, 9.

According to another aspect of the invention, a medium pressure distillation stage (DIS.MP) is introduced which is fed through line 3' from stripper (ST).
- Given the presence of this new distiller (DIS.MP), operating for example at about 18–22 bar, the urea solution leaving the stripper (ST) will have a greater amount of carbamate and NH3 than the design value. Together with the increased yield in the reactor, the stripper's (ST) (and the carbamate condenser's CO.CA) heat load can be reduced appreciably with the possibility, therefore, of overloading them as compared to the design load.
- The urea solution (SU) leaving the stripper (ST) is distilled in the new MP distiller (DIS) up to a residual amount of carbamate and NH3 lower than the design amount. This in turn reduces the heat load of the subsequent stage (DIS.LP) of distillation L.P., thus allowing an increased load in respect of the design value.
- According to a further advantage of the invention the vapors leaving the new distiller (DIS.MP) (consisting of NH3, CO2, H2O) are condensed, according to the double-effect technique, in a new pre-evaporator (Pr.EV) situated in series with the existing evaporator (EV1) of the 1st vacuum stage, operating at for example 0.35 bar a.

In this way the condensation heat of the vapors mentioned (Vu) is used to concentrate the urea solution (SU) permitting a considerable heat recovery, while at the same time reducing the heat load in the existing evaporator (EV1).
- This last fact makes it therefore possible not only to open up the space for a possible overloading of the existing evaporator EV1 compared to design conditions, but also to "force" the degree of distillation of the solution so that the heat load of the existing vacuum evaporator (EV2) can be made lighter thus allowing it to be overloaded in respect of its design value.

The importance of the invention for the modernization of stripping plants with CO2 becomes therefore evident, especially where the increase in capacity is concerned.

As regards the passivation stage or system it is worth noting that it can be effected according to the known technique, an d more particularly according to the method described in European patent 0096151.

In this patent a method is described to eliminate corrosion in the stripping equipment of urea plants operating at high temperature and pressure and in contact with an evaporating process fluid in the liquid state, such stripping being carried out in at least one stage and with at least a stripping agent chosen from CO2 or NH3 at a pressure between 120 and 240 bar; the method is characterized by the fact that for the protection of the strippers' metal surfaces a passivating system is used, injecting oxygen in synergic combination with a liquid agent or in a solution chosen from the group consisting of H2O2, nitrites (alkaline, alkaline ammonic), persulphate (alkaline or ammonic), alkaline perborate, peracetic acid and organic peroxide.

In the embodiment exemplified (applied to the protection of metal walls in austenitic stainless steel) the passivating combination results from putting together: O2 from 500 to 2000 ppm (with respect to the fed CO2) and H2O2 in amounts corresponding to a content of active oxygen between 1 and 25 ppm, preferably 2 and 10, and even better between 4 and 6 ppm in respect of the global flow of the process fluid.

Belgian patent 625.397 also describes a method for passivating the internal surfaces of a urea synthesis reactor using oxygen as the passivating agent and suggesting it be replaced at least partially with other passivating agents such as H2O2 alkaline or alkaline-earth peroxides. This method which seemed to have solved the problem of corrosion in reactors where the process fluid is substantially in the liquid state, has proved however insufficient for the strippers where corrosion reaches a very high level because the process fluid is present as an evaporating liquid and temperatures may be higher than those in the reactor.

The present state of the technique seems to suffer from a few contradictions. The second prior art reference suggested a method which, although suitable for the reactor, was inadequate for the strippers. The first prior art document certainly solved this last problem but does not seem to cover entirely the whole system.

This and other drawbacks of the known technique mentioned may be found in the fact that previously the problem of corrosion was dealt with on its own, isolating it from the rest of the problems and leaving unexplored the possibility of studying whether it could be solved in a wider context. In fact in the two previous patents efforts are made to solve only the problem of corrosion, admitting that there are gradients of the corrosion phenomenon for example going from its values in the reactor and other parts of equipment to the higher values in the stripper.

To this diversity of position other difficulties are added: in effect the amounts of oxygen (even if combined with H2O2) have been determined keeping in mind the requirements of passivation only and omitting to study whether those optimal figures where corrosion was concerned did not introduce secondary effects unhelpful where other characteristics of the process are concerned. In other words, in the state of the art the aim has been almost exclusively the elimination of corrosion, so that there seems to be a lack of teaching regarding the opportunity of exploring whether passivation measures may be considered flexibly within the framework of a system of modernization for the entire plant, and thus be coordinated with measures concerning yield, consumption, flexibility etcetera.

In the overall view according to the invention it has been ascertained, for example, that if as the determining parameter for the purpose of an optimal treatment the residence time of the process products in contact with the surfaces of the equipment is assumed, passivation can be effected in the most selective and efficient manner.

For example, where said residence times are below about 30 seconds as in the stripper, the amount of H2O2 must be kept in the high area whereas the O2 must be kept in the low area of the preferred respective intervals; in this way with reference to preferred intervals according to the European patent above-mentioned, i.e. for the H2O2 between 4 and 6 ppm and O2 between 500 and 2000, we have seen that for residence times for example shorter than 30 seconds the H2O2 may be kept at 4 ppm and the O2 may actually be lower than the bottom limit of 500 ppm.

On the other hand, where residence times are greater, as for example at 30 seconds, H2O2 may be made lower than the lowest value and be kept for example between 0 and 2 ppm and O2 is above 2000.

At the limit, the synergie mixture H2O2+O2 (air) may be introduced where there is permanence and in that case O2 will not be, preferably, above 500 ppm. Where, on the contrary, the amount of H2O2 is lowered (or even eliminated) a certain amount of O2 may be introduced above 2000, or even critically equal to 2500 ppm. These indications apply above all to those plants where stripping is effected with synthesis CO2, i.e. feeding air to the reactor with the compressor for the synthesis CO2, first through the stripper and then to the reactor.

If self-stripping is carried out, i.e. the feed CO2 does not run through the stripper but goes directly to the reactor, the amounts of O2 and/or H2O2 may be selected differently.

We claim:

1. A process for modernizing an existing urea plant to increase urea yield of the plant, reduce energy consumption by the plant and inhibit corrosion within the plant, the plant including a reactor for synthesizing urea from ammonia and carbon dioxide, a stripper for stripping product leaving the reactor with a reagent, a condenser for condensing carbamate out of an ammonia feed stream for the reactor, a scrubber for treating vapors leaving the reactor, means for introducing an amount of passivating air into the stripper, scrubber and condenser, a decomposer for decomposing products of the stripper, and an evaporator, the modernization process comprising the steps of:

introducing an oxidizing agent into the plant at a location in the plant upstream of the stripper and condenser, the oxidizing agent being in a liquid phase;

increasing the molar ratio of ammonia to carbon dioxide within the reactor to produce an excess of ammonia in the reactor of between 2.8 and 3.4 mol while reducing the amount of passivating air in the stripper, scrubber and condenser by about ⅓;

distilling products from the stripper at medium pressure between 6 and 50 bar in a medium pressure distillation means located between the stripper and the decomposer, and condensing vapors produced by the distillation in a pre-evaporator at low pressure, said pre-evaporator being located downstream of the medium pressure distillation means and in series with a first vacuum stage of the evaporator.

2. The process according to claim 1, wherein the reagent is carbon dioxide.

3. The process of claim 1, wherein the oxidizing agent is hydrogen peroxide.

4. The process of claim 1, wherein the stripper products are distilled at a pressure between 12 and 30 bar.

5. The process of claim 4, wherein the stripper products are distilled at a pressure between 18 and 22 bar.

6. The process of claim 1, wherein the vapors produced by the medium pressure distillation are condensed in the pre-evaporator at 0.35 bar.

7. A modernized plant for the preparation of urea, comprising:

a) an existing urea preparation plant including:
      1) a high pressure loop including:
         i) a reactor for synthesizing the urea from ammonia and carbon dioxide;
         ii) a stripper for stripping product leaving the reactor with a reagent;
         iii) a condenser for condensing carbamate from an ammonia feed stream for the reactor; and
         iv) a scrubber for treating vapors exiting the reactor;
      2) a low pressure loop including:
         i) a decomposer for decomposing products of the stripper; and
         ii) an evaporator;
   b) a medium pressure distillation means located between the stripper and the decomposer for distilling urea solution produced by the stripper and thus reducing heat load in the stripper and the decomposer;
   c) a pre-evaporator located downstream of the medium pressure distillation column and in series with a first vacuum stage of the evaporator for concentrating the urea solution using the condensation heat of vapors from the medium pressure distillation section; and
   d) means for introducing an oxidizing agent into the plant at a location in the plant upstream of the stripper and the condenser.

* * * * *